(12) United States Patent
Saylor et al.

(10) Patent No.: US 7,106,300 B2
(45) Date of Patent: Sep. 12, 2006

(54) METHOD FOR CONVERTING JOYSTICK DEFLECTION INTO MOTION IN A COMPUTER VISION SYSTEM

(75) Inventors: Barry E. Saylor, Kent, WA (US); Rodney B. Doe, Seattle, WA (US); Mark Delaney, Shoreline, WA (US)

(73) Assignee: Mitutoyo Corporation, Kawasaki (JP)

( * ) Notice: Subject to any disclaimer, the term of this patent is extended or adjusted under 35 U.S.C. 154(b) by 363 days.

(21) Appl. No.: 10/195,689

(22) Filed: Jul. 12, 2002

(65) Prior Publication Data

US 2004/0008181 A1    Jan. 15, 2004

(51) Int. Cl.
*G09G 5/08* (2006.01)
*G05B 1/06* (2006.01)

(52) U.S. Cl. ...................... 345/161; 318/640
(58) Field of Classification Search ................ 345/161, 345/156–166; 702/188, 150; 219/121.63; 359/630; 339/630; 318/592, 640, 466
See application file for complete search history.

(56) References Cited

U.S. PATENT DOCUMENTS

| 4,223,257 | A |   | 9/1980 | Miller |  |
|---|---|---|---|---|---|
| 5,677,709 | A | * | 10/1997 | Miura et al. | 345/161 |
| 6,002,995 | A | * | 12/1999 | Suzuki et al. | 702/188 |
| 6,377,904 | B1 | * | 4/2002 | Yamashita | 702/150 |
| 6,596,961 | B1 | * | 7/2003 | Ehlers et al. | 219/121.63 |
| 6,614,596 | B1 | * | 9/2003 | Gladnick | 359/630 |

FOREIGN PATENT DOCUMENTS

| JP | 08-086965 | 4/1996 |
|---|---|---|
| JP | 9127426 | 5/1997 |

OTHER PUBLICATIONS

Description of QUICK VISION™ and QVPAK™ products available from Mitutoyo American Corporation, 1 pg.

* cited by examiner

*Primary Examiner*—Sumati Lefkowitz
*Assistant Examiner*—Srilakshmi K. Kumar
(74) *Attorney, Agent, or Firm*—Christensen O'Connor Johnson Kindness PLLC

(57) ABSTRACT

A method is provided for converting joystick deflection into a speed of relative motion between a image system and a workpiece stage in a computer vision system. The conversion of joystick deflection into speed may be described in terms of a speed/deflection profile that corresponds a present lens characteristics of the system. In one embodiment, the speed/deflection response of the system depends relatively strongly on the present lens characteristic at relatively lower deflections and depends on relatively weakly on the present lens characteristic as the deflection approaches a maximum deflection. The system is advantageous in that, for any lens used, it maintains consistent ergonomic and visual feel at small joystick deflections which typically occur during ostensible precision maneuvers, but is also able to provide fast long-range traverses for large joystick deflections.

20 Claims, 14 Drawing Sheets

METHOD FOR CONVERTING JOYSTICK DEFLECTION INTO MOTION IN A COMPUTER VISION SYSTEM

FIELD OF THE INVENTION

The invention relates generally to methods for operating a computer vision system to scan and measure an object, and more particularly to a method for converting deflection of a joystick or other manual control device into motion in a computer vision system.

BACKGROUND OF THE INVENTION

Computer vision systems can be utilized to obtain precise dimensional measurements of inspected objects. Such systems may include a computer and a camera and optical system with a stage that is movable to allow the camera to scan the surface of an object that is being inspected. One exemplary prior art system that is commercially available is the QUICK VISION™ series of vision inspection machines and QVPAK™ software available from Mitutoyo America Corporation (MAC), located in Aurora, Ill. This product is able to provide images of an object at various magnifications, and move the stage as necessary to traverse the object surface beyond the limits of any single video image. A single video image typically encompasses only a portion of the object being observed or inspected, given the desired magnification, measurement resolution and physical size limitations of such systems.

Visions systems such as Quick Vision™ are generally designed to facilitate industrial inspection. Such systems frequently include a lens turret with lenses of various magnifications. It is common to inspect various aspects of a single object using the various magnifications. Furthermore, in industrial inspection environments, very large inspection objects are common, and dimensions to be measured often extend beyond a field of view. In such systems, a convenient and ergonomically intuitive manual motion control system that consistently addresses all the above factors is of great utility.

In contrast, in conventional laboratory vision systems which utilize microscopes, a single video image may often encompass an entire object or the object may extend a relatively small distance outside the filed of view, given the generally small size of objects observed by such systems. Some systems include a manual motion control system that responds to manual input, and the response to the input is linearly scaled according to a selected magnification. The joysticks in certain other systems include a contact switch which triggers high speed motion at large deflections.

An example of a vision system utilizing a microscope that includes dual joystick control modes for inspection and manipulation of relatively small objects is shown in U.S. Pat. No. 5,677,709. The system of the '709 patent teaches a joystick which controls a micromanipulator which is used to three dimensionally position an object in the field of the microscope. The system can be operated in a speed control mode and a position control mode. In the speed control mode an actuator is driven by a speed corresponding to the inclined amount of the manipulating lever for the joystick. In the position control mode, the actuator is driven by a distance corresponding to the inclined amount of the manipulating lever of the joystick. The system switches between the speed control mode and the position control mode according to a change-over switch. One of the problems that the '709 patent addresses is that when the mode is switched from the position control mode to the speed control mode while the joystick is inclined, the system will be started in motion even if this was not the intent of the operator. The '709 system avoids this problem by only switching between the modes when the joystick is in the neutral position. While the method of the '709 patent addresses certain issues regarding switching between modes in a joystick controlled microscope vision system, it still requires switching between the two modes in an inconvenient manner. In addition, none of the above systems offer a robust and appropriate method for manually controlling the motion axis of a machine vision system that alters the focus of the system.

The present invention is directed to providing a method that overcomes the foregoing and other disadvantages. More specifically, the present invention is directed to a method for converting the deflection of joystick or other manual control device into motion which uses speed/deflection profiles that are selected in accordance with the present lens characteristics of the system.

SUMMARY OF THE INVENTION

A method for converting joystick deflection into motion in a computer vision system is provided. In accordance with one aspect of the invention, the conversion of joystick deflection into speed is done according to a speed/deflection profile that is selected in accordance with a current lens characteristic of the system, such as a magnification ratio and/or a depth of field, or any other appropriate lens parameter or combination of parameters indicative of an observable imaging property of the lens. In one embodiment, the speed/deflection profiles are designed so that at lower deflection ranges the speed/deflection profiles are at least partially based on a formula that includes the present lens characteristic as a factor, while at higher deflection ranges, the speed/deflection profiles are designed to become primarily independent of the lens characteristic, and thus allow for fast long-range movement regardless of the present lens characteristic. The speed/deflection profiles may generally be non-linear in nature and the relationship between different speed/deflection profiles may generally be non-linear in nature.

In accordance with another aspect of the invention, the speed/deflection profiles may generally be for movement of the stage in either the focal plane direction/axes (X-Y axes) or the focus direction/axis (Z axis). The focus axis of a vision system is often much shorter than the X-Y axes. Furthermore, for short working distance lenses, there is a significant risk that the user may accidentally cause the lens to collide with the work piece during a Z-axis motion. Thus a maximum speed in the focus direction may be less than a maximum speed for moving in the X-Y plane.

In accordance with another aspect of the invention, for higher ranges of joystick deflection, the speed/deflection profiles may approach a common transport speed, which is the maximum speed for navigating the stage of the vision system. For machines that can operate in an automatic mode, for example under computer program control, the transport speed may be different depending on whether the manual or automatic control mode is being used. The transport speed of the automatic control mode may be higher than that of the manual control mode, in that the automatic control mode is generally less likely to drive the stage in a manner that could cause damage to the system.

It will be appreciated that the disclosed method for converting joystick deflection into motion is advantageous in that the system factors in lens characteristics such as magnification and/or depth of field at small joystick deflections which typically occur during ostensible precision maneuvers, and also is able to move rapidly (for providing fast long-range traverses) for large joystick deflections. It will also be appreciated that in various exemplary embodiments the disclosed method is advantageous in that the method provides an intuitive and consistent ergonomic feel in relation to a video display of the image seen by the vision system camera, regardless of the lens in use.

These advantages represent significant improvements over prior vision systems, such as those which included a manual motion control system that responded linearly to manual input, and those which were scaled linearly according to a selected magnification. Such systems provide either insufficient low speed selectivity or tediously slow top speed or both when applied to the microscopic inspection of large objects. In the prior systems which included a joystick with a contact switch which triggered high speed motion at large deflections, in addition to switch cost and reliability concerns, it was difficult to avoid ergonomically disconcerting results with the use of the contact switch, especially when applying a variety of magnifications to the microscopic inspection of large objects in a single vision system. Similarly, the prior dual mode systems which could be operated in a speed control mode and a position control mode, also did not address the issues related to position control in larger vision systems, where larger objects and distances between objects may require rapid movement over large distances while still requiring more precise movements over selected magnified areas of an object. As noted above, all of these issues are addressed by the various aspects of the present invention.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
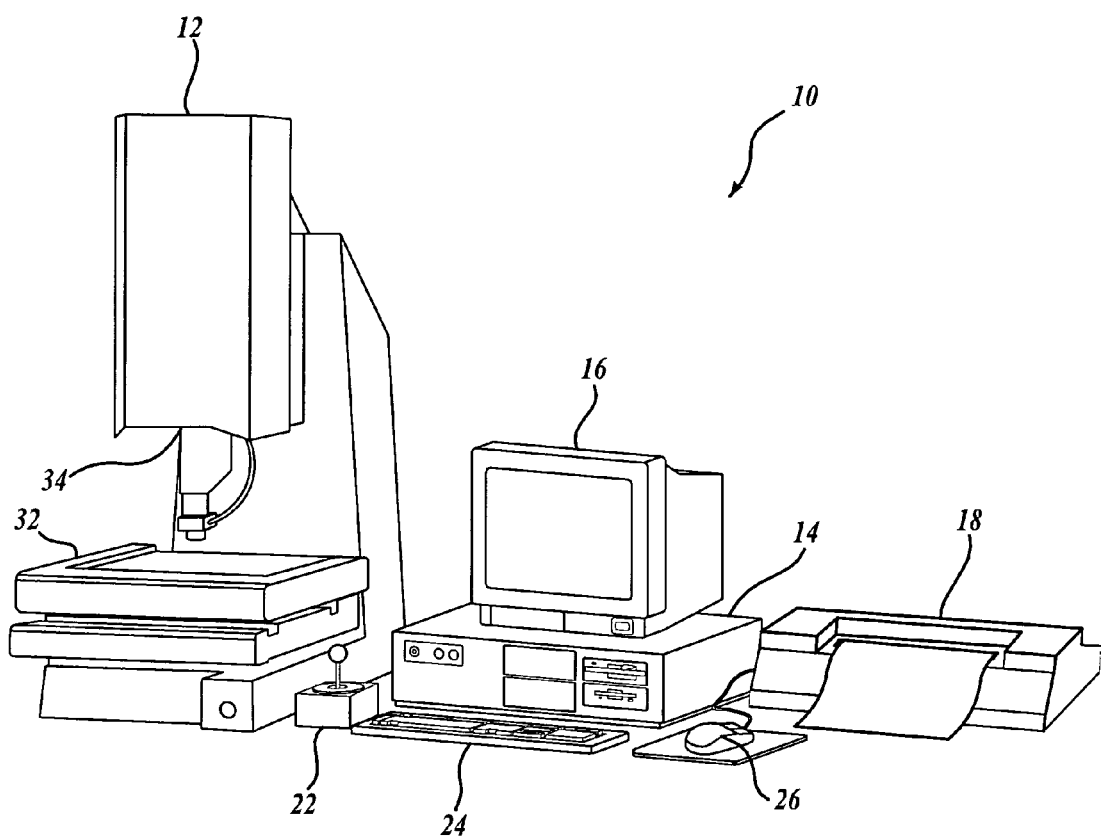
FIG. 1 is a block diagram of a vision system including a joystick control.

FIG. 1 is a block diagram of one exemplary vision system 10 in accordance with the present invention. Vision system 10 includes a vision measuring machine 12 that is operably connected to exchange data and control signals with a controlling computer system 14. The controlling computer system 14 is further operably connected to exchange data and control signals with a monitor 16, a printer 18, a joystick 22, a keyboard 24, and a mouse 26. The vision measuring machine 12 includes a moveable workpiece stage 32 and an optical imaging system 34 which includes interchangeable lenses. The interchangeable lenses generally provide various magnifications for the images provided by the optical imaging system 34.

In various exemplary embodiments the optical imaging system 34 includes a zoom lens system that provides the functional equivalent of a variety of interchangeable lenses. It should be appreciated that for a zoom lens systems, the magnification may be varied continuously. Generally, as the magnification is varied, the depth of field may also vary. It will be appreciated that for any particular zoom lens system the magnification and/or depth of field can be determined based on the lens configuration at any particular time. In turn, the lens configuration can generally be determined by monitoring the position of one or more of the zoom lens elements with displacement sensors, or by inference from the lens configuration control signals sent to a motion subsystem that alters the lens configuration. In any case, the magnification and/or depth of field or the like provided by any zoom lens configuration can be readily determined. Thus, according to this invention, the lens characteristics associated with each configuration of a zoom lens can be determined and each configuration of a zoom lens provides a functional equivalent to an interchangeable discrete lens.

The amount of various deflection components of the handle of the joystick 22 can typically be used to control the movement direction components of the movable workpiece stage 32 in both the X and Y directions, which are generally parallel to the focal planes of the optical imaging system 34, and the movement direction component of the movable optical imaging system 34 in the Z or focus direction. Frequently, the deflection that controls the Z axis is a rotary deflection component of a handle or knob of the joystick 22. It will be appreciated that the joystick 22 may be provided in a form other than that shown, such as any visual representation or widget on the monitor 16 which is intended to function as a "virtual motion control device" of the vision system 10 and is controllable through any computer input device such as the mouse 26 or the like.

In should also be appreciated that in various other vision systems, one, two or three axes of relative motion between a workpiece stage and an optical imaging system may be provided by other combinations of movable axes, and the orientation of the camera may be horizontal or even angled. However, regardless of the configuration of a vision system, in the following discussion X and Y axes or directions lie in a plane that is generally parallel to the focal planes of the optical imaging system of the vision system, and the Z or focus axis or direction is generally parallel to the focus axis of the optical imaging system of the vision system.

It will be appreciated that the controlling computer 14 includes control software and/or hardware for controlling the operations of the vision measuring machine 12, as exemplified by the general design and software architecture of various commercially available machine vision systems. In particular, the control software and/or hardware includes a motion control portion and an input device deflection converter portion and/or routine. The deflection converter portion receives deflection information from a joystick or the like, and provides appropriate corresponding control information to the motion control system.

In some deflection converter routines, each of the physical joystick deflection components are modeled as a fraction δ of full joystick deflection for that component such that $-1 <= \delta <= 1$. The resultant motion is a function $f(\delta, V_{max})$, where Vmax is a maximum speed. One example of such a function is:

$$V(\delta) = \delta^3 V_{max} \quad \text{(Eq. 1)}$$

With the above Equation 1, given a 25% deflection, and a $V_{max}$ of 100 mm/sec, the resultant speed $V(\delta)$ would be $(0.25)^3 \times 100 = 1.56$ mm/sec. This may generally work well at 1× magnification, but at 60× magnification, the field of view and/or "image pixels" (meaning specific bits of an image that are of a size corresponding to one pixel on a display of the image) would move by at the same rate as if a 1× magnification image were moving at over 90 mm/sec. This makes precise navigation difficult to impossible at higher magnifications.

For better fine-level control, it would be preferable if the joystick deflection converter would consider lens magnification at small values of δ. To achieve this, one could simply scale the joystick response in a manner inversely proportional to the magnification. An equation illustrating this is:

$$V(\delta, mag) = (\delta^3 V_{max})/mag \quad \text{(Eq. 2)}$$

Equation 2 scales the controlled speed inversely to the magnification, that is, for higher magnifications, the stage will move slower for a given deflection. Thus, a magnified image on a set of camera pixels will tend to traverse a the camera pixels or a corresponding display at the same "image pixel rate", or "portion of view rate", for low deflections δ, regardless of magnification. Such rates are conveniently referred to as ergonomically relevant "image change rates." However, a drawback with Equation 2 is that the top controllable speed is also reduced. This needlessly slows down long-range stage traverses, for example for the purpose of locating a new portion of a large workpiece, or a new workpiece in an array of workpieces, in the field of view.

It would be preferable if the joystick deflection converter would consider lens magnification at small values of δ, during ostensible precision maneuvers, but tend to ignore lens magnification and move rapidly (for providing fast long-range traverses) for high levels of δ. It is possible to achieve both objectives. One example is illustrated by the following equation:

$$K(\delta, mag, N) = mag - (|\delta|^N (mag - mag_{baseline})) \quad \text{(Eq. 3)}$$

At zero joystick deflection (δ=0), the second term in Equation 3 resolves to zero, and K then resolves to mag. At other low joystick deflections (δ=0.1, 0.2, etc), the second term in Equation 3 remains small, and K is approximately mag. For larger joystick deflections (δ=0.7, 0.8, etc), the second term in Equation 3 becomes significant, and K begins to deviate from mag and approach $mag_{baseline}$. For full joystick deflection (δ=1.0), K resolves to $(mag - mag + mag_{baseline}) = mag_{baseline}$.

If Equation 3 is modified to use the K function in place of mag in Equation 2, the following equation results:

$$V(\delta, mag) = (\delta^3 V_{max})/K \quad \text{(Eq. 4)}$$

$$V(\delta, mag) = (\delta^3 V_{max})/[mag - (|\delta|^N (mag - mag_{baseline}))] \quad \text{(Eq. 5)}$$

Equation 5 provides an equation for speed as a function of joystick deflection and lens magnification. For low values of δ, that is, for relatively low speeds appropriate for relatively precise operations, the denominator of the above Equation 5 approaches the lens magnification, yielding an ergonomically consistent image change rate, that is, a consistent image pixel rate for a given small δ for any lens magnification. For high values of δ, the denominator approaches $mag_{baseline}$, a constant value allowing a consistent high speed regardless of magnification. Equation 5 also provides a relatively smoothly varying control function that results in an ergonomically intuitive feel over the full range of joystick deflections. In certain embodiments, these are all considered to be desirable joystick behaviors.

In various embodiments according to this invention, $mag_{baseline} = 1$, making the high speed equal to $V_{max}$. More generally, $mag_{baseline}$ can be any value corresponding to the lowest magnification lens in the system, and $V_{max}$ may be scaled with a corresponding coefficient value. In such a case, any higher magnification lens will have a top speed the same as the top speed associated with the lowest magnification lens in the system, regardless of its value.

Regarding the exponent N, it can be seen that the second term in Equation 3 has a decreasing effect for low values of δ, as N increases. This results in the joystick behavior being similar (in terms of magnified image pixels) for low values of δ. However, as δ approaches 1, the exponent value becomes irrelevant—thus maintaining the desired behavior.

Figure 2:
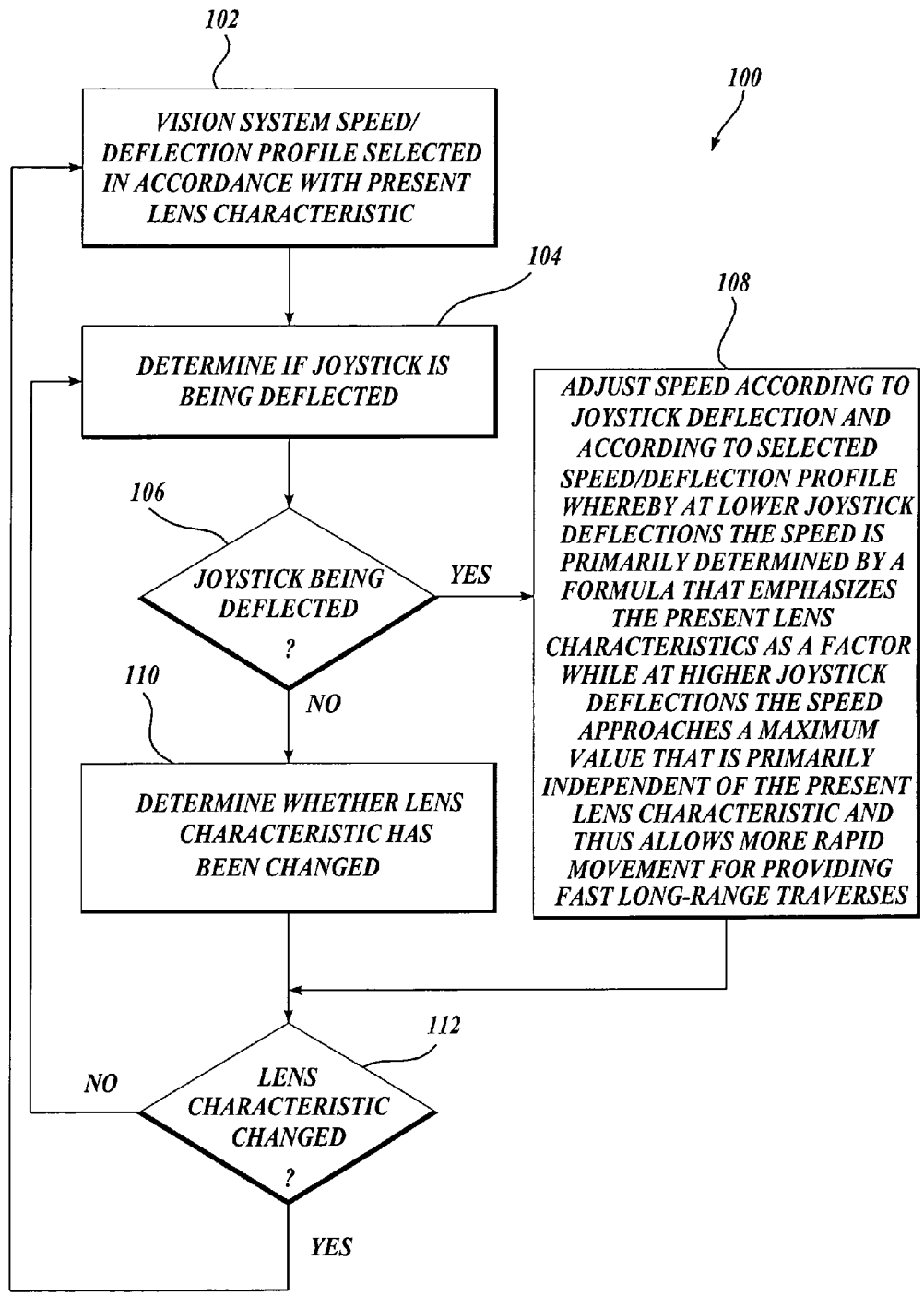
FIG. 2 is a flow diagram illustrating a general method of converting joystick deflection into speed in a vision system.

FIG. 2 is a flow diagram illustrating one exemplary routine 100 usable for converting the deflection of a joystick or other input device into speed in a vision system. It should be appreciated that the flow diagram of FIG. 2 is applied to each respective component or "axis" of joystick deflection corresponding to a respective axis of motion control. Therefore, for each respective axis, the flow diagram of FIG. 2 refers to the respective lens characteristic and the respective speed/deflection profile appropriate to that axis. In various embodiments, the X and Y axes are controlled according to the same lens characteristic and speed/deflection curve. However, it should be appreciated that in various embodiments the Z axis is controlled by a separate lens characteristic and speed/deflection curve, as described further below.

As shown in FIG. 2, at a block 102 the speed/deflection profile is selected in accordance with a present lens characteristic of a present lens in use in the image system. As will be described in more detail below, in one embodiment the speed/deflection profiles may generally be either X-Y axis or Z axis (a.k.a. focus axis) speed/deflection profiles. As will also be described in more detail below, the speed/deflection profiles are generally non-linear in that at low joystick deflections, the speed is primarily determined by a formula dependent on the lens characteristic, and at higher joystick deflections the speed approaches a maximum value that is primarily independent of the lens characteristic.

At a block 104, the routine determines if the joystick is being deflected along the respective axis. As noted above, the joystick may also be in other forms, such as a virtual joystick on the vision system monitor. At a decision block 106, the routine evaluates whether the joystick was determined to be deflected at block 104. If the joystick was being deflected, then the routine continues to a block 108, where the speed is adjusted according to the joystick deflection and according to the speed/deflection profile that was selected at block 102. The routine then continues to a block 110, which will be described in more detail below.

If at block 106 the routine determines that the joystick is not being deflected, then the routine continues to block 110. At block 110, the routine determines whether the lens characteristic, which was the basis for selecting the speed/deflection profile at block 102, has been changed. For example, the vision system may determine this based on a current lens identity provided by a lens turret position, or user input, or any other now known or later developed lens identity determining method or method that determines a lens characteristic directly by analyzing optical system behavior. At block 112, the routine evaluates whether the determination at block 110 was that the lens characteristic has changed. If the lens characteristic has not changed, then the routine returns to block 104. If the lens characteristic has changed, then the routine returns to block 102.

Figure 3A:
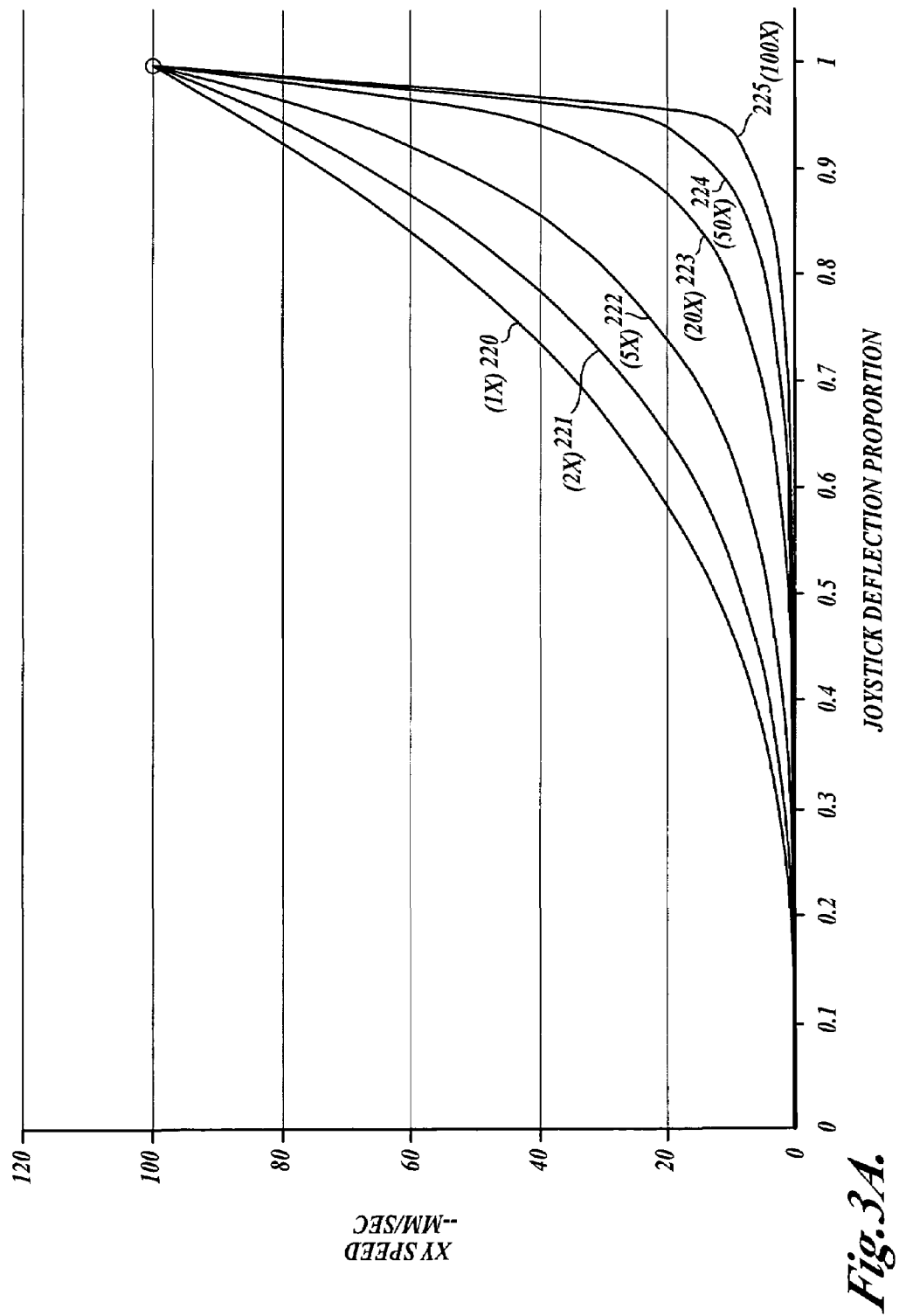
FIG. 3A is a control curve diagram illustrating X-Y axis speed/deflection profiles according to the magnification ratios of selected lenses.
Figure 3B:
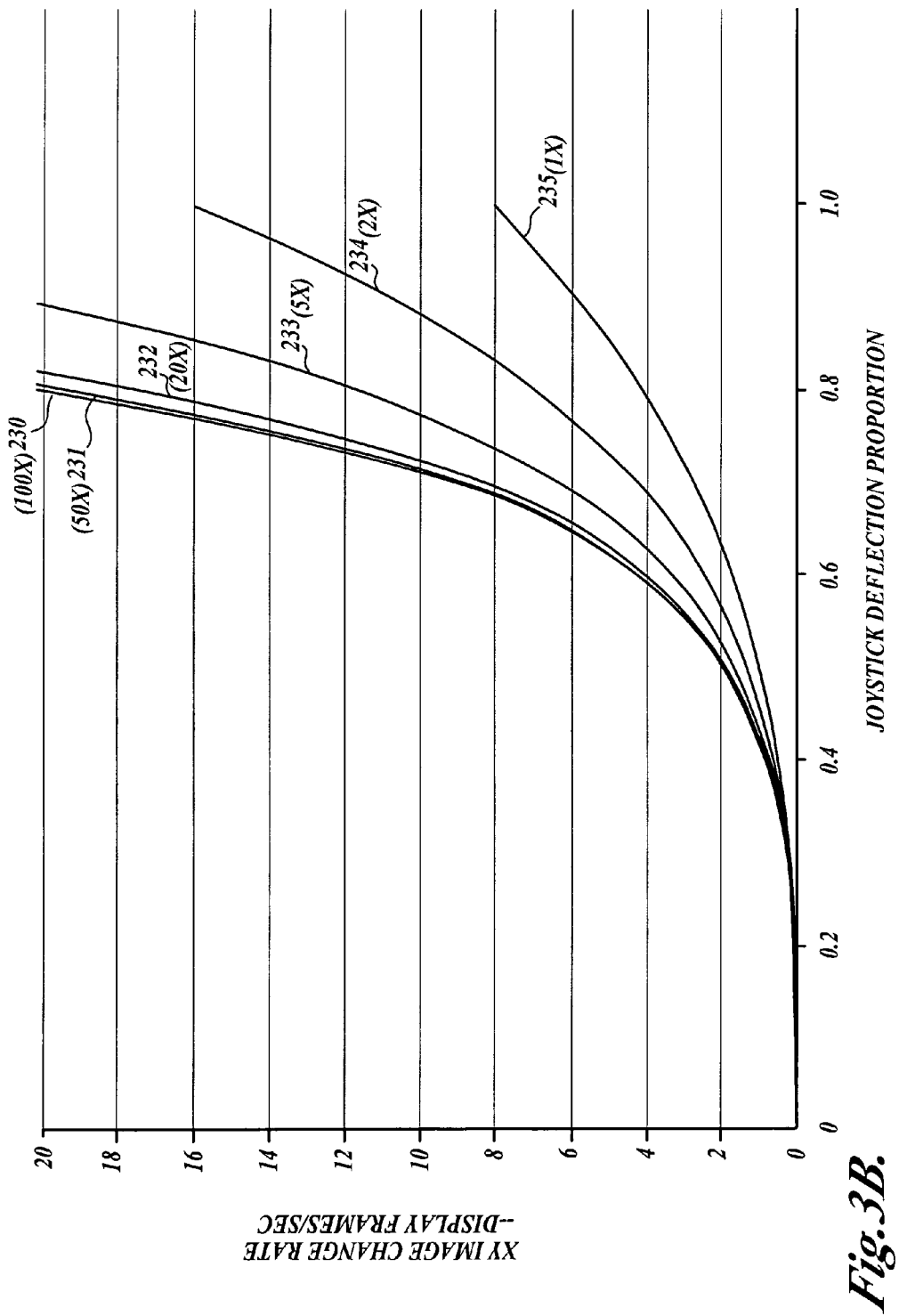
FIGS. 3B–3D are diagrams illustrating the results of the X-Y axis speed/deflection profiles of FIG. 3A, in terms of various image change rates.
Figure 3C:
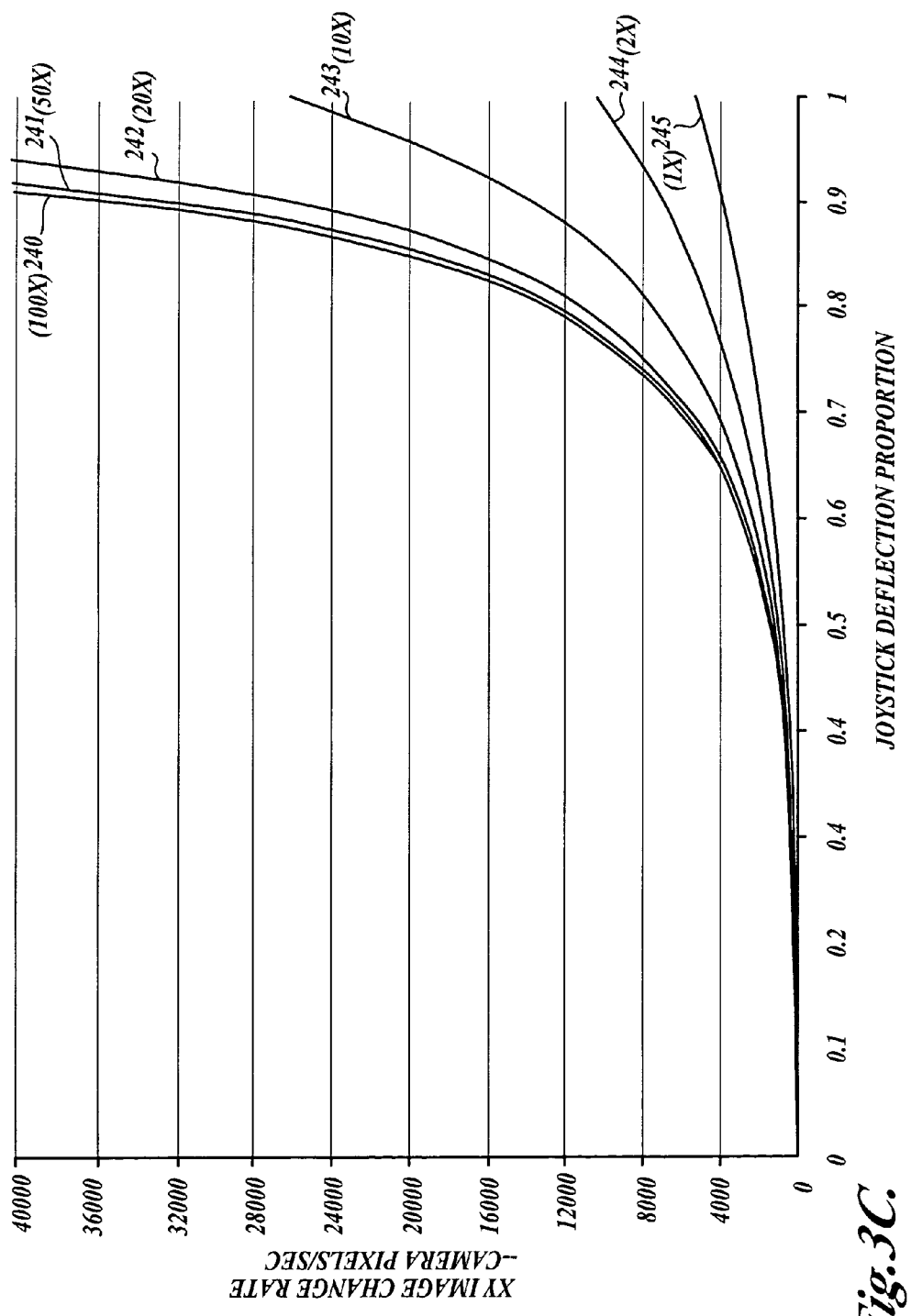
Figure 3D:
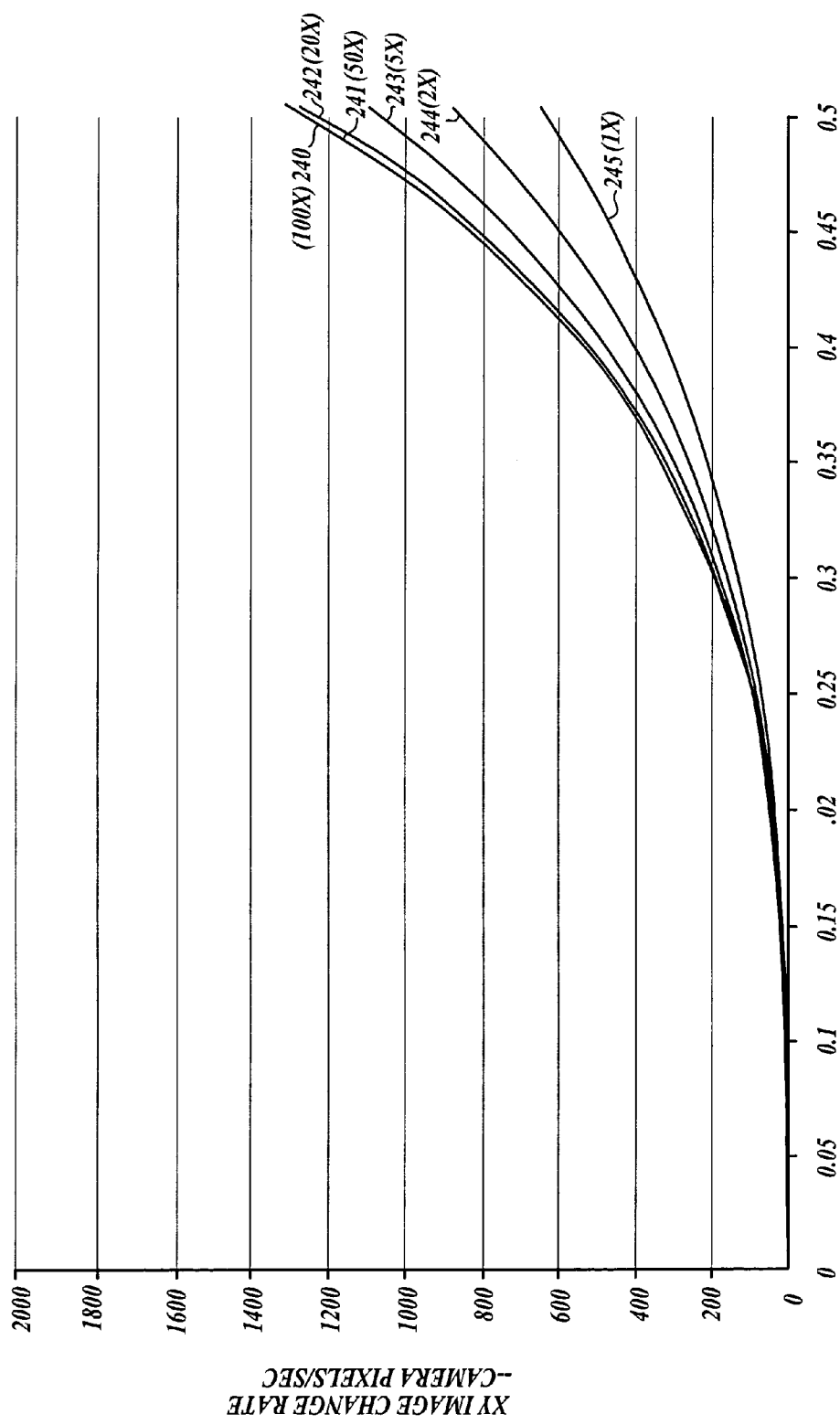
Figure 4A:
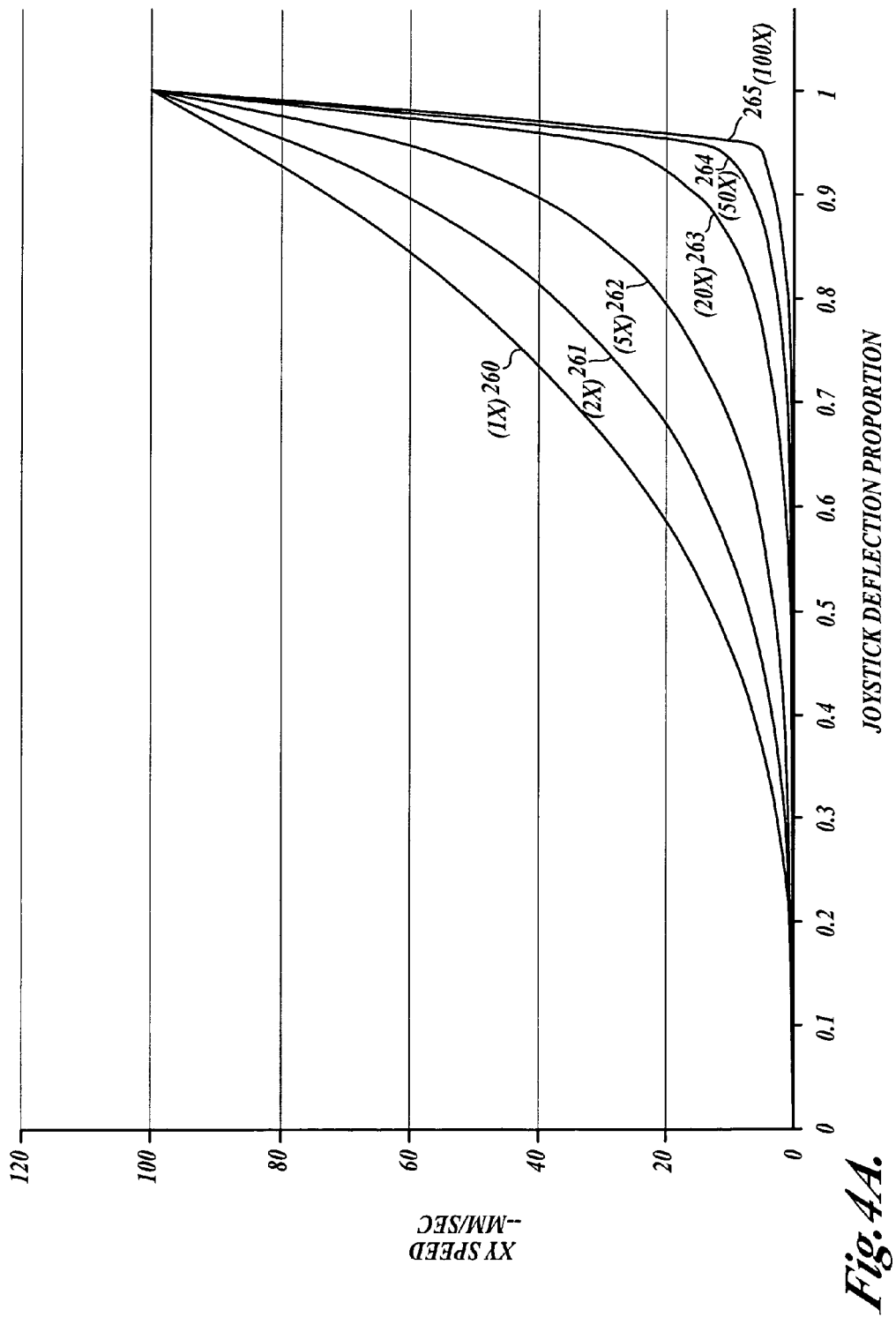
FIG. 4A is a control curve diagram illustrating alternate X-Y axis speed/deflection profiles according to the magnification ratios of selected lenses.

FIGS. 3A and 4A illustrate X-Y speed/deflection profiles usable in conjunction with the exemplary routine 100, or more generally as a basis for any control system that controls vision system motion based on joystick deflection. The lens characteristic corresponding to the illustrated X-Y speed/deflection profiles is the magnification ratio of selected lenses. For the magnification ratio of each selected lens, the profiles relate a level of joystick deflection to the corresponding X-Y speed that is to be produced. FIGS. 3B–3D and 4B–4D illustrate the results of the X-Y axis speed/deflection profiles of FIGS. 3A and 4A, respectively, in terms of various ergonomically relevant image change rates.

Each of the FIGS. 3A–3D and 4A–4D include six curves corresponding to six magnification ratios of six selected lenses, including magnification ratios of 1×, 2×, 5×, 20×, 50×, and 100×. For the six 1× to 100× curves in each of the FIGS. 3A–3D, the curves correspond to setting the parameters in Equation 5 as follows: $N=1$, $mag_{baseline}=1$, $mag=$ each respective lens magnification ratio, and $V_{max}=100$ mm/s. For each of the six 1× to 100× profiles in each of the FIGS. 4A–4D, the curves correspond to the same parameters, except $N=2$. It should be appreciated that when even powers are used for exponents, the equation is valid for positive joystick deflections, and a symmetric negative-direction speed response results is provided based on a negative deflection of the joystick.

FIG. 3A shows six speed/deflection profiles 220–225, and FIG. 4A shows six speed/deflection profiles 260–265 corresponding, respectively, to the six magnification ratios 1×, 2×, 5×, 20×, 50×, and 100×, corresponding to six selected lenses. The profiles relate the joystick deflection proportion to the X-Y speed in millimeters per second, to emphasize that a maximum transport speed is independent of the selected lens, while the speed changes smoothly throughout the control range. As illustrated in the profiles, as the joystick deflection proportion approaches its maximum value, the speed approaches a "transport speed" which is the maximum speed for navigating the large stage of the vision system. As shown, each of the profiles approaches a transport speed of 100 millimeters per second, which generally occurs at the full joystick deflection proportion of 1.

It will be appreciated that the transport speed may be different depending on whether a manual or automatic control mode is being used. For example, in an embodiment where FIG. 3A represents X-Y speed/deflection profiles for a manual mode and the transport speed in the manual control mode is 100 millimeters per second, in an automatic control mode the transport speed may be higher (e.g., 200 millimeters per second). The transport speed of the automatic control mode may be higher than that of the manual control mode, in that the automatic control mode may be less likely to drive the stage in a manner that could cause damage to the system.

Figure 4B:
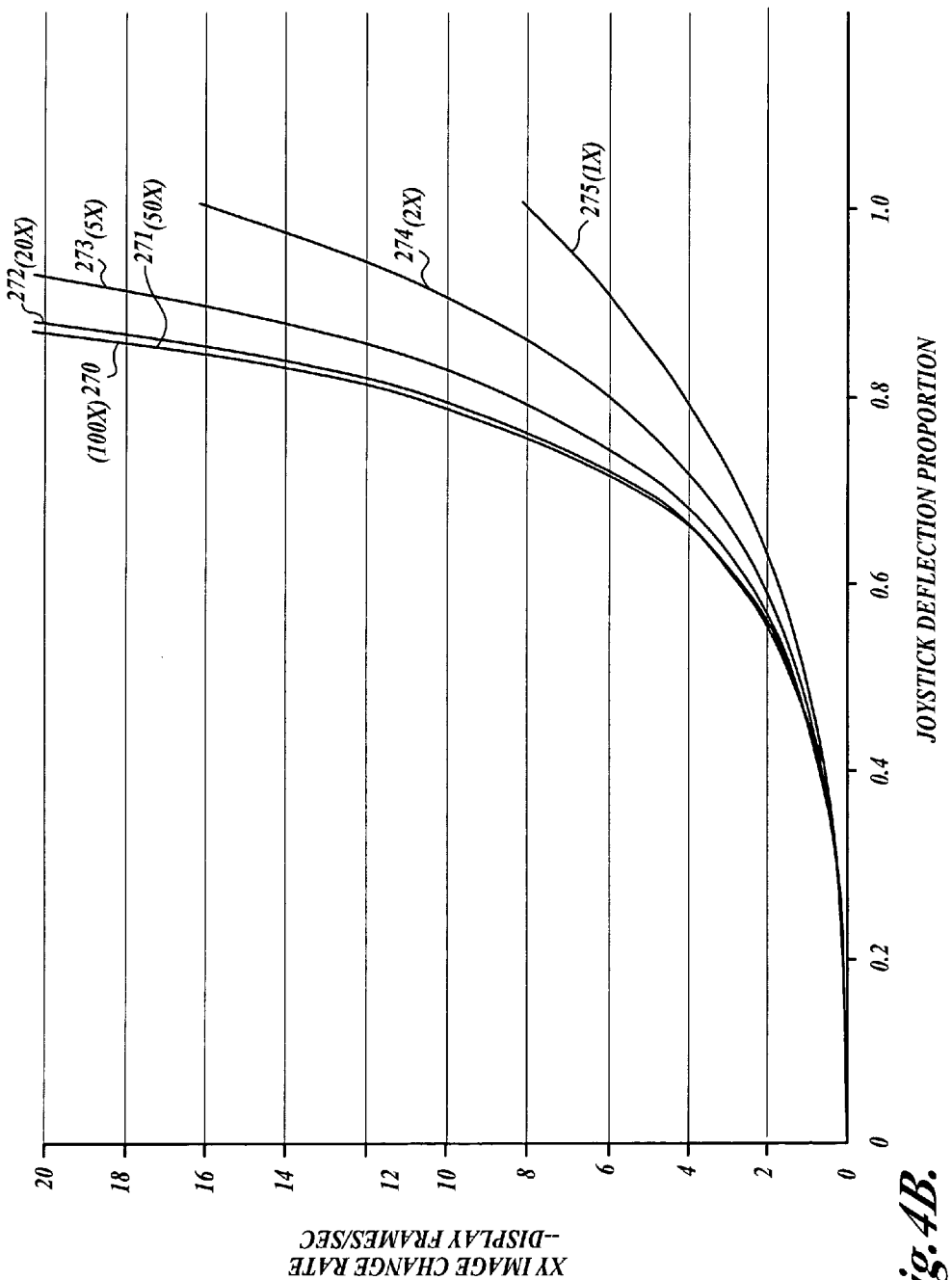
FIGS. 4B–4D are diagrams illustrating the results of the alternate X-Y axis speed/deflection profiles of FIG. 4A, in terms of various image change rates.

FIG. 3B shows six image change rate/deflection curves 230–235, and FIG. 4B shows six image change rate/deflection curves 270–275, corresponding, respectively, to the six magnification ratios 1×, 2×, 5×, 20×, 50×, and 100×, corresponding to the six selected lenses. In one embodiment, the vision system camera has 640×480 pixels covering the microscopic field of view, and the display frame shows the same number of pixels. The curves relate the joystick deflection proportion to the X-Y speed in display frames per second to emphasize an image change rate that is one important ergonomic factor. It should be appreciated that the curves show that over a substantial range of smaller deflections used for relatively precise control, the image change rate is similar for a given joystick deflection regardless of the selected lens. That is, an image feature will traverse a video display frame at approximately the same rate for a given joystick deflection regardless of the selected lens. Generally, this substantial range includes and exceeds the deflections and/or speeds that might be used during relatively precise positioning or searching operations by a user. At larger deflections the increase in image change rate will vary as needed to reach the desired maximum transport speed. As noted above, at higher magnification ratios, a smaller amount of an object is actually displayed, and thus may require many display frames to view the entire surface of an object.

Figure 4C:
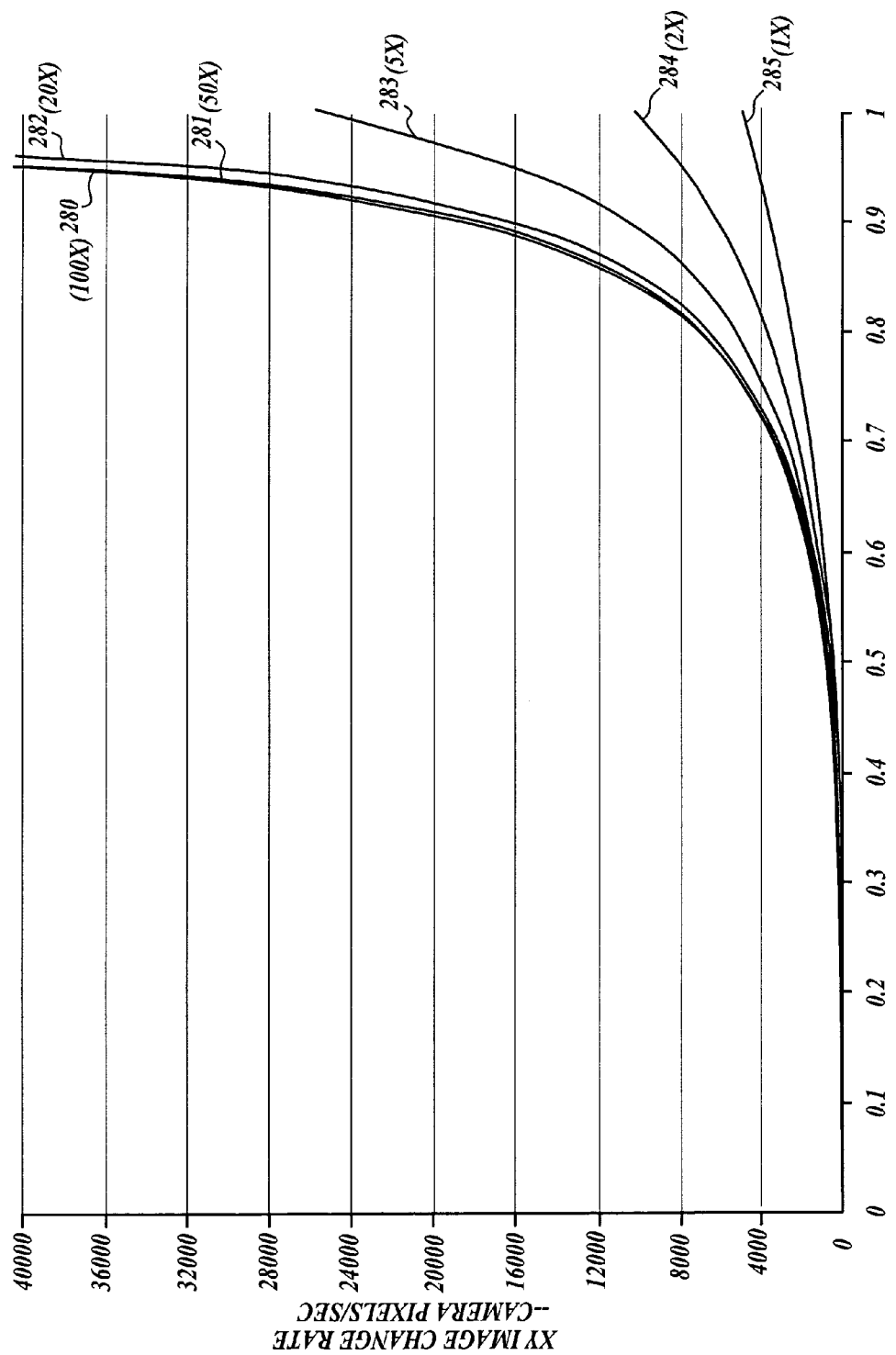

FIG. 3C shows six image change rate/deflection curves 240–245, and FIG. 4C shows six image change rate/deflection curves 280–285, corresponding, respectively, to the six magnification ratios 1×, 2×, 5×, 20×, 50×, and 100×, corresponding to the six selected lenses. The curves relate the joystick deflection proportion to the X-Y speed in camera pixels per second to emphasize that the same ergonomic considerations and outcomes discussed above with reference to FIGS. 3B and 4B apply more generally to the image changes rates such as the field of view of any camera, or indeed to the field of view available to the naked eye through a microscope objective.

Figure 4D:
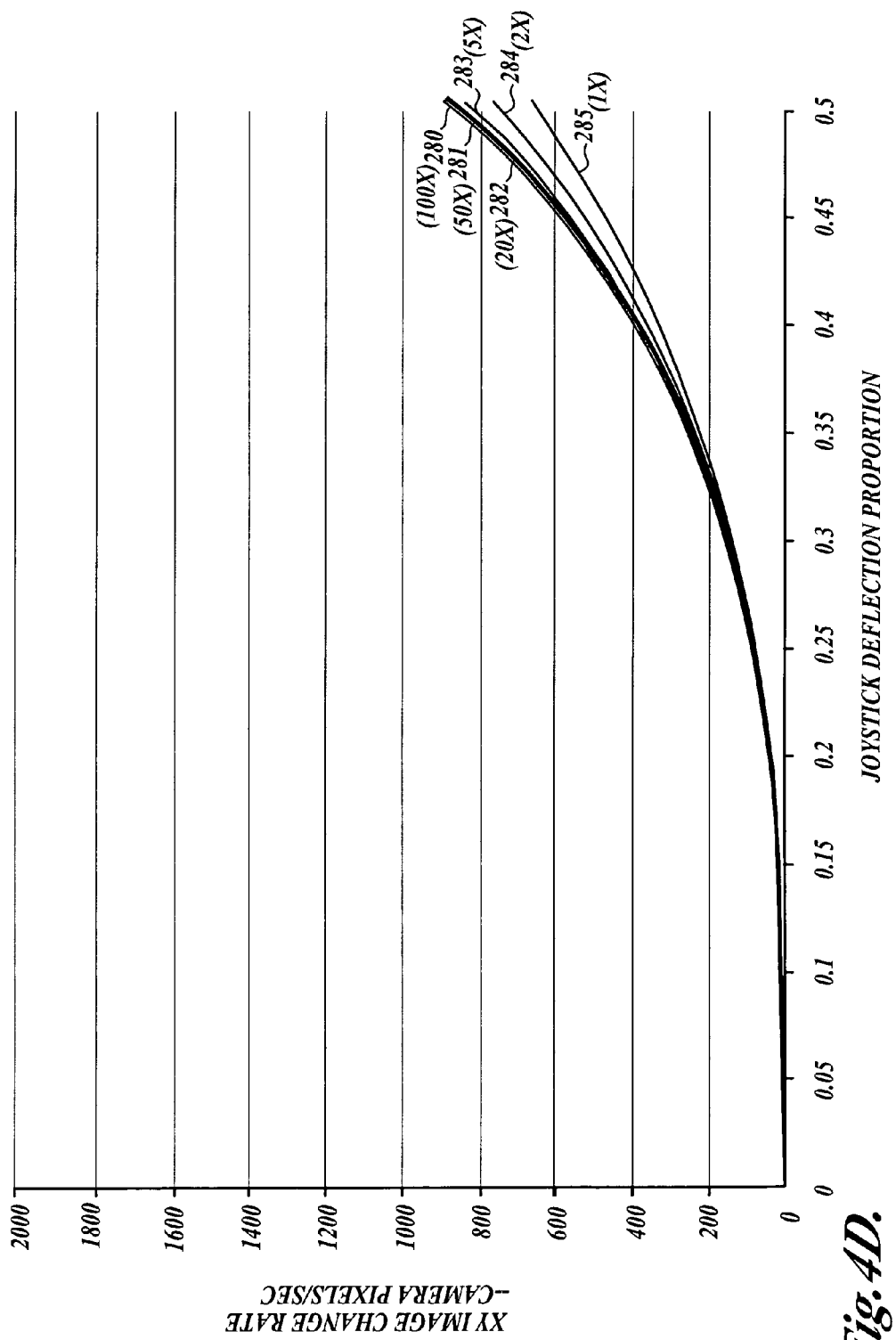

FIGS. 3D and 4D each show six curves which are respectively the same as the corresponding curves of FIGS. 3C and 4C for joystick deflection proportions of 0 to 0.5, rather than 0 to 1.0, thus providing a more detailed version of this range that can be more easily viewed. Corresponding curves have corresponding reference numbers.

The differences between the profiles and results of FIGS. 3A–3D and FIGS. 4A–4D should be appreciated. By setting $N=1$ in Equation 5 to generate the profiles and results of FIGS. 3A–3D, the range of smaller deflections wherein an image feature will traverse a frame at a relatively constant pixel rate or image change rate is relatively reduced while the transition to the transport speed is made relatively smoother for higher magnifications. In contrast, by setting $N=2$ in Equation 5 to generate the profiles and results of FIGS. 4A–4D, the range of smaller deflections wherein an image feature will traverse a frame at a relatively constant pixel rate or image change rate is relatively increased while the transition to the transport speed is made relatively sharper for higher magnifications. However, more generally, it should be appreciated that other profiles according to the principles of this invention may be generated by setting N equal to other values greater than zero and N is not restricted to integer values. Furthermore, it should be appreciated that the exponent "3" on the first occurrence of deflection δ in Equation 5 could more generally be any value greater than 1, and is not restricted to integer values. In general, the choice between such tradeoffs is made based on ergonomic experiments and/or user preferences.

The rate at which the focus of an image changes is related to the Z-axis control of the vision system. It should be appreciated that the magnification of a lens is reliably related to the X-Y dimensions in the resulting image, while for various lenses the relationship between the magnification and focusing characteristics of each lens is generally unpredictable. Thus, the following analysis for the focus speed and focus range is analogous to the X-Y speed and range analysis that was discussed above, except that for controlling the focus axis, the "visible range" is related more directly to the depth of field (DOF) characteristic of the lens, rather than to the magnification. The DOF is conventionally defined as:

$$DOF = \lambda * n / (NA^2) \tag{Eq. 6}$$

Where λ is the wavelength of illuminating light (e.g., white light at 555 nm), n is the refractive index of the medium (usually air (1.000)) between the workpiece and the objective front lens element, and NA equals the numerical aperture of the objective lens. The image generally becomes blurry one DOF beyond the plane of best image focus (in either direction).

Thus, for better fine-level focus control, it is preferable for the joystick deflection converter control corresponding to the focus direction to consider lens DOF. To achieve a consistent ergonomic feel related to the rate of focus change of an image, one method would be to scale the response to a Z axis joystick deflection δ in a manner proportional to the DOF of the current lens relative of the DOF of a baseline lens having a relatively large DOF. That is, the Z axis speed may be a function $V_z$ as follows, where $V_{max}$ is a maximum Z axis speed:

$$V_z(\delta, DOF_{current}) = (\delta^3 V_{max}) * (DOF_{current}/DOF_{baseline}) \tag{Eq. 7}$$

Equation 7 scales the controlled speed proportionally to the current DOF, that is, for smaller DOF's (generally, higher magnifications have smaller DOF's, but not in proportion to their relative magnifications) the stage will move slower for a given deflection. Thus, an "in focus" region will tend to be traversed at the same focus-traverse rate for low deflections δ regardless of the lens DOF (or magnification). However, a drawback with Equation 7 is that the top controllable speed is also reduced. This needlessly slows down long-range focus changes, for example for the purpose of locating a new surface or workpiece in the present field of view, or in a new field of view.

It is preferable for the joystick deflection converter to consider lens DOF at small values of δ, during ostensible precision maneuvers, but to ignore lens DOF and move quickly (for providing fast transport to inspection targets located at a different heights) for high levels of δ. It is possible to achieve both objectives. One example is illustrated by the following equation:

$$K_z(\delta, DOF_{current}, N) = DOF_{current} - (|\delta|^N (DOF_{current} - DOF_{baseline})) \tag{Eq. 8}$$

At zero joystick deflection (δ=0), the second term in Equation 8 resolves to zero, and $K_z$ then resolves to $DOF_{current}$. At other low joystick deflections (δ=0.1, 0.2, etc), the second term in Equation 8 remains small, and $K_z$ is approximately $DOF_{current}$. For larger joystick deflections (δ=0.7, 0.8, etc), the second term in Equation 8 becomes significant, and $K_z$ begins to deviate from $DOF_{current}$ and approach $DOF_{baseline}$. For full joystick deflection (δ=1), $K_z$ resolves to $(DOF_{current} - DOF_{current} + DOF_{baseline}) = DOF_{baseline}$.

If Equation 7 is modified to use the $K_z$ function in place of $DOF_{current}$:

$$V_z(\delta, DOF_{current}) = (\delta^3 V_{max}) * (K_z/DOF_{baseline}) \tag{Eq. 9}$$

$$V_z(\delta, DOF_{current}) = (\delta^3 V_{max}/DOF_{baseline}) * [DOF_{current} - (|\delta|^N (DOF_{current} - DOF_{baseline}))] \tag{Eq. 10}$$

The result is an equation for speed as a function of joystick deflection and lens DOF. For low values of δ, that is, for relatively low speeds appropriate for relatively precise operations, the multiplier in the above Equation 10 approaches the current lens DOF, yielding an ergonomically consistent focus range traverse rate for a given small δ regardless of the lens DOF. For high values of δ, the multiplier approaches $DOF_{baseline}$, providing a constant value for $V_z$, allowing a consistent high speed regardless of the lens DOF. In certain embodiments, these are all considered to be desirable joystick behaviors. Equation 10 also provides a relatively smoothly varying control function that results in an ergonomically intuitive feel over the full range of joystick deflections. In certain embodiments, these are all considered to be desirable joystick behaviors. In general, $DOF_{baseline}$ can be any value, but is usually chosen corresponding to the largest DOF lens in the system. In such a case, any lens having a smaller DOF will have a top speed the same as the top speed associated with the largest DOF lens in the systems, regardless of its DOF value.

Regarding the exponent N, it can be seen that the second term in Equation 8 has a decreasing effect for low values of δ, as N increases. This results in the joystick behavior being similar (in terms of focus-traverse rate) for low values of δ. However, as δ approaches 1, the exponent value becomes irrelevant—thus maintaining the desired behavior.

Because the DOF is usually a small dimension, in some embodiments, it is useful to control the speed according to a $4^{th}$-power function of deflection. That is:

$$V_z(\delta, DOF_{current}) = (\delta^4 V_{max}/DOF_{baseline}) * [DOF_{current} - (|\delta|^N (DOF_{current} - DOF_{baseline}))] \tag{Eq. 11}$$

It should be appreciated that when even powers are used for exponents, the equation is valid for positive joystick deflections, and a symmetric negative-direction speed response is provided based on a negative deflection of the joystick.

Figure 5A:
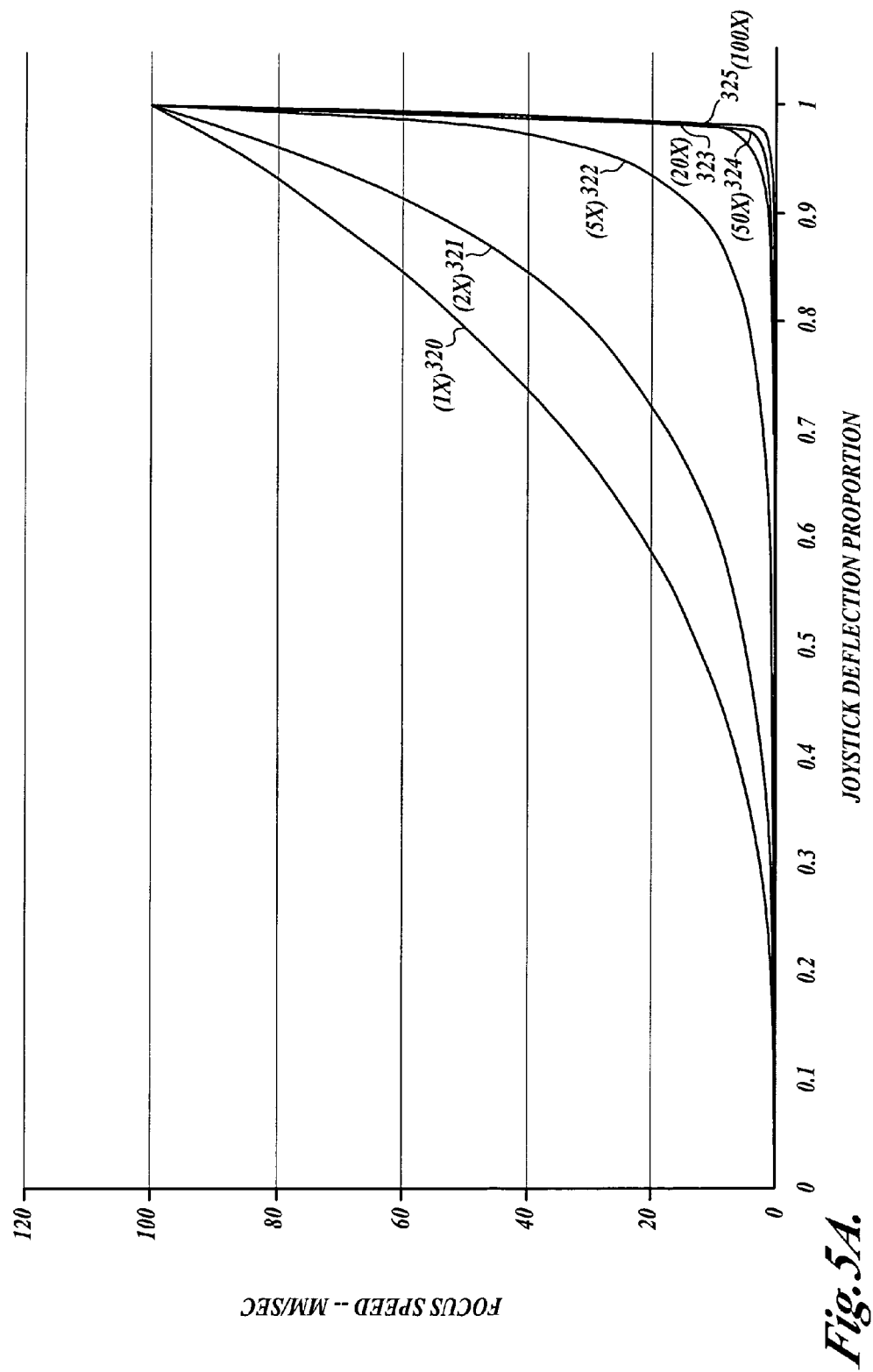
FIG. 5A is a control curve diagram illustrating focus axis speed/deflection profiles according to the depth of field provided by selected lenses.
Figure 5B:
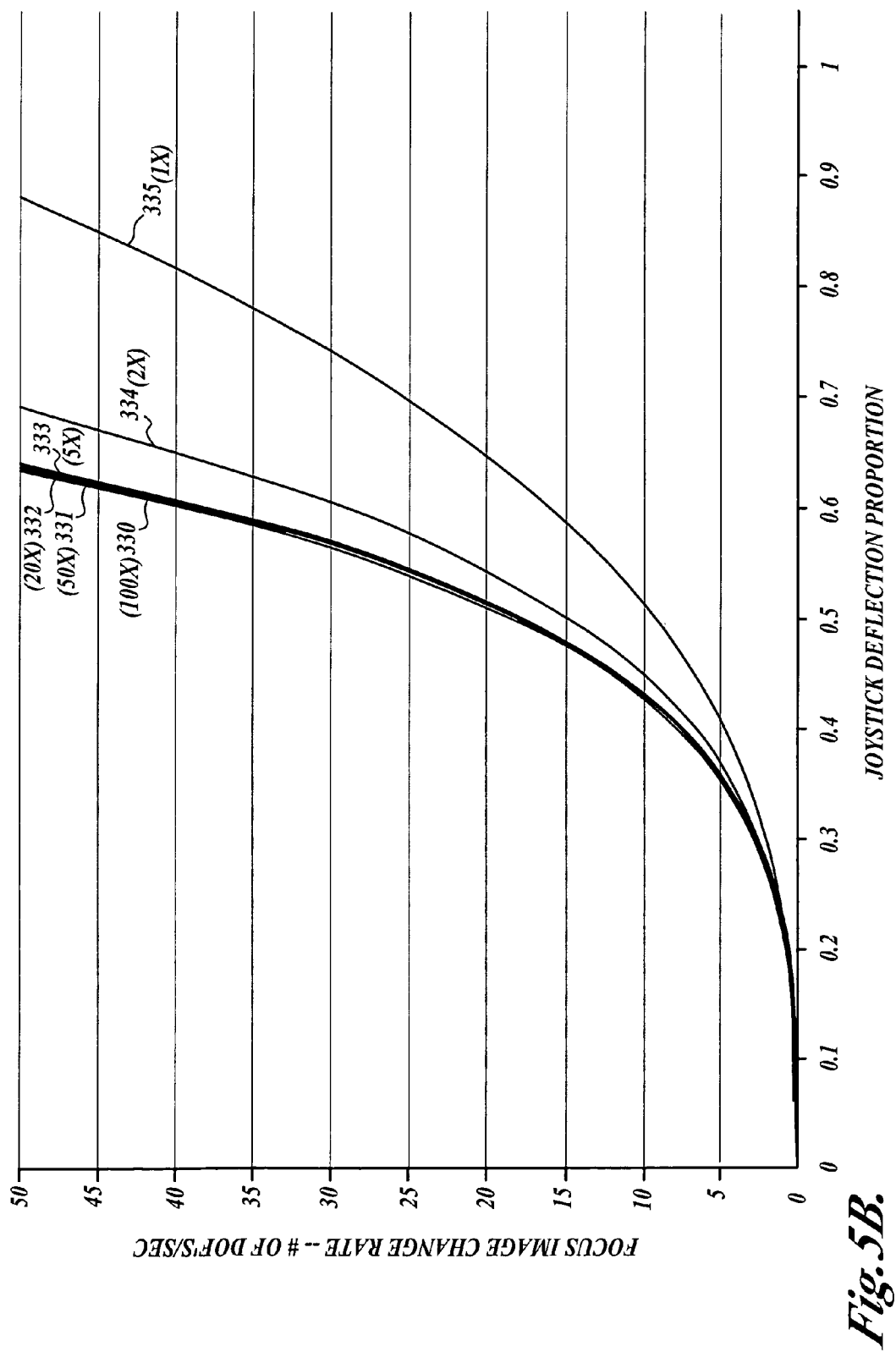
FIG. 5B is a diagram illustrating the results of the focus axis speed/deflection profiles of FIG. 5A, in terms of the focus image change rate.
Figure 6A:
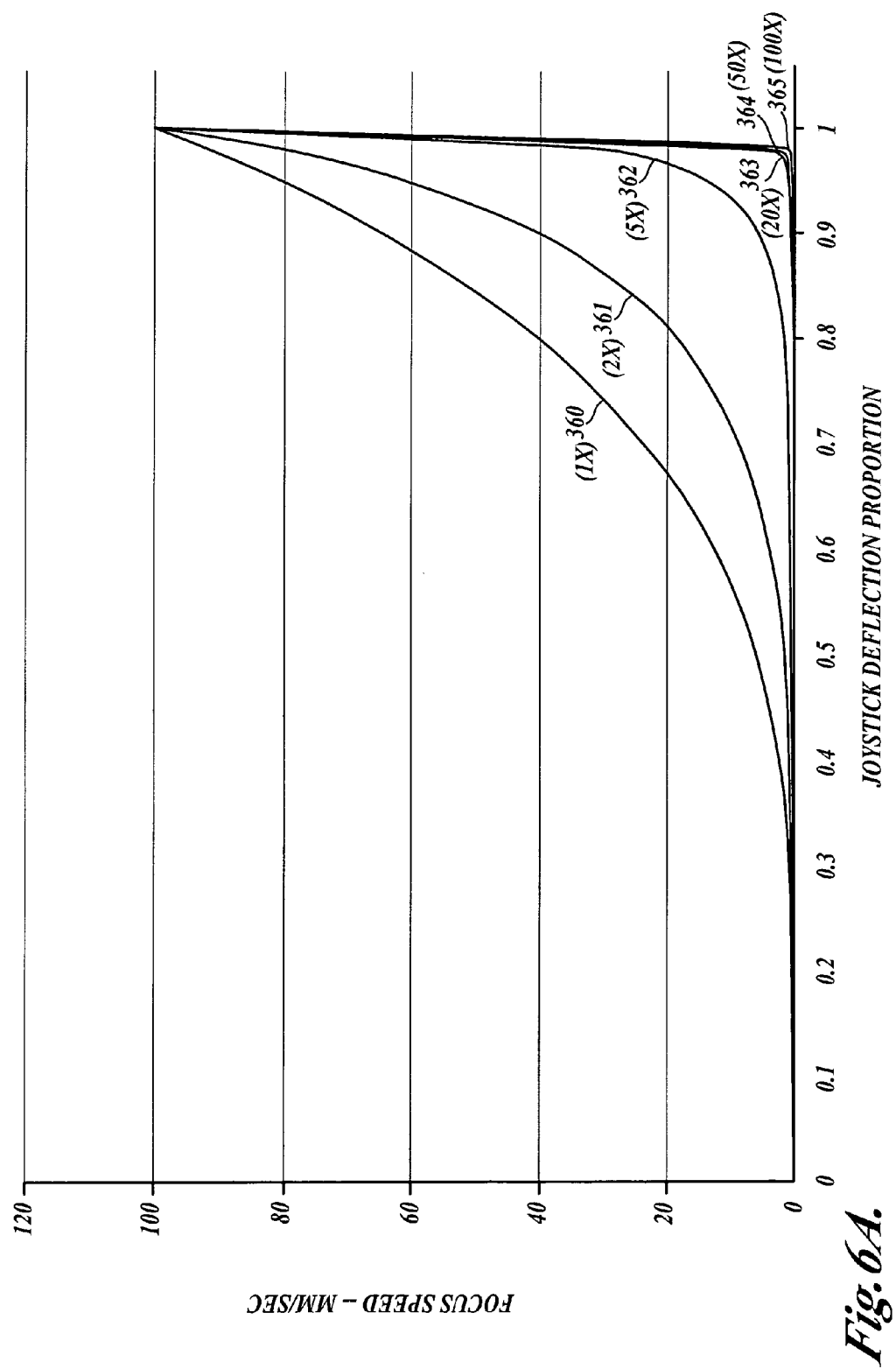
FIG. 6A is a control curve diagram illustrating alternate focus axis speed/deflection profiles according to the depth of field provided by selected lenses.
Figure 6B:
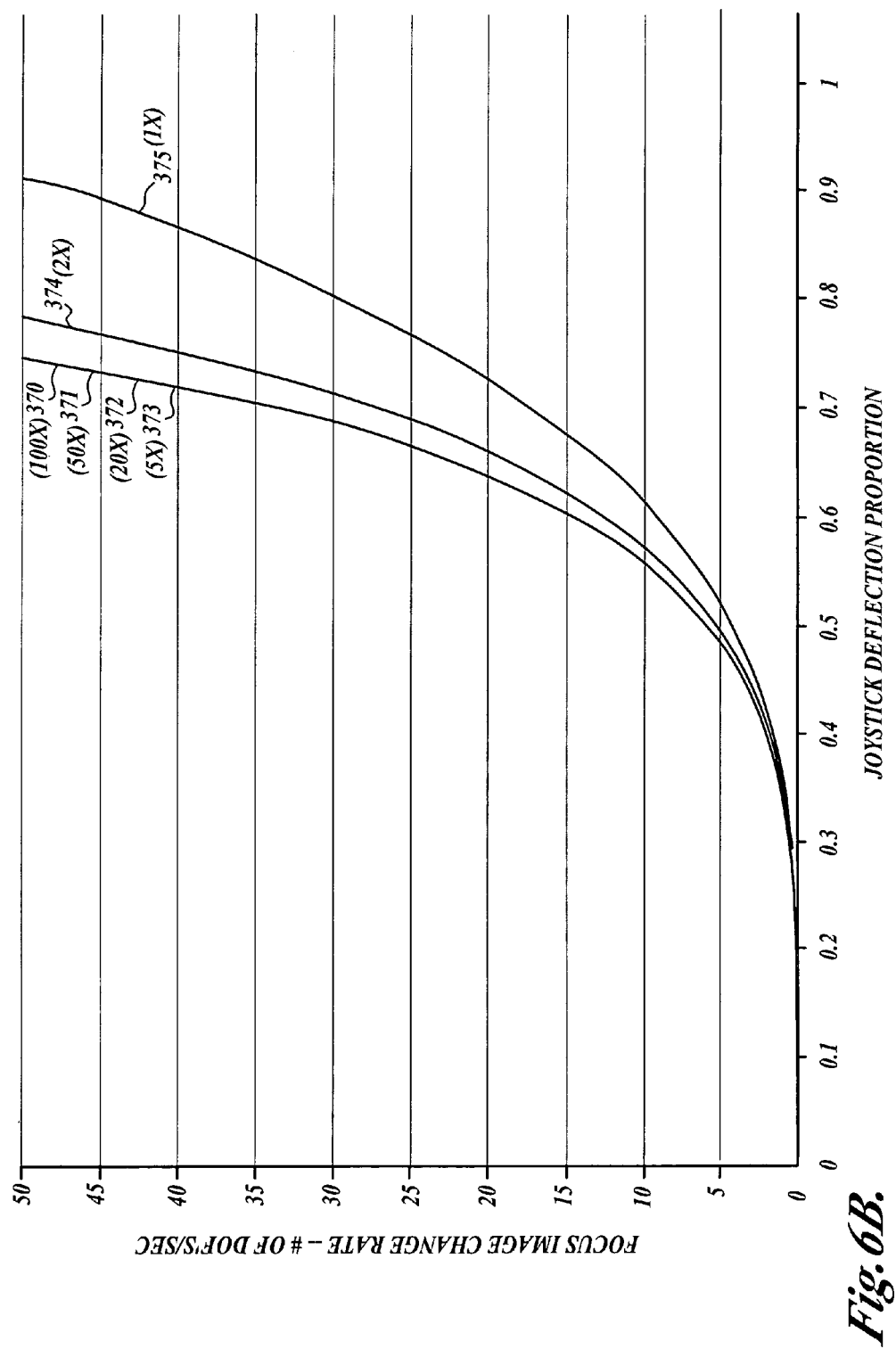
FIG. 6B is a diagram illustrating the results of the alternate focus speed/deflection profiles of FIG. 6A, in terms of the focus image change rate.

FIGS. 5A and 6A illustrate focus axis speed/deflection profiles usable for focus axis control in conjunction with the exemplary routine 100, or more generally as a basis for any control system that controls vision system focus axis motion based on joystick deflection. It should be appreciated that although the selected lens is conveniently identified by its magnification value in FIGS. 5–6, the lens characteristic corresponding to the illustrated Z axis focus speed/deflection profiles is the DOF of selected lenses. For the DOF of each selected lens, the profiles relate a level of joystick deflection to the corresponding Z axis speed that is to be produced. FIGS. 5B and 6B illustrate the results of the Z axis speed/deflection profiles of FIGS. 5A and 6A, respectively, in terms of ergonomically relevant focus image change rates. In each of the FIGS. 5A–5B and 6A–6B there are six curves corresponding to six DOF's of six selected lenses, identified by their magnifications of 1×, 2×, 5×, 20×, 50×, and 100×.

For each of the six 1× to 100× curves in each of the FIGS. 5A–5B, the curves correspond to setting the parameters in Equation 10 as follows: N=1, $DOF_{baseline}$=the DOF of the 1× lens, $DOF_{current}$=each respective lens DOF, and $V_{max}$=100 mm/s. Exemplary DOF's in mm for the various lenses are as follows, 1×DOF=1.34, 2×DOF=0.323, 5×DOF=0.028, 20×DOF=0.0031, 50×DOF=0.0018 and 100×DOF=0.0011. For each of the six 1× to 100× profiles in each of the FIGS. 6A–6B, the profiles correspond to using Equation 11 with the same parameters, except setting N=2. It should be appreciated that when even powers are used for exponents, the equation is valid for positive joystick deflections, and a symmetric negative-direction speed response results is provided based on a negative deflection of the joystick.

FIGS. 5A–5B and 6A–6B are similar to FIGS. 3A–3B and 4A–4B, described above, except FIGS. 5A–5B and 6A–6B relate the joystick deflection proportion to focus axis speed and image change rate, rather than to X-Y axis speed and image change rate. Focus axis speed may also be referenced as a type of Z-axis speed. As shown in FIGS. 5A and 6A, based on the depth of field characteristic of each selected lens, the profiles relate a level of joystick deflection to the corresponding focus axis speed that is produced. In each of the FIGS. 5A and 6A, there are six speed/deflection profiles corresponding, respectively, to the depth of field characteristics of six selected lenses. The selected lenses are conveniently identified by their respective magnifications of 1×, 2×, 5×, 20×, 50×, and 100×.

FIG. 5A shows six focus speed/deflection profiles 320–325, and FIG. 6A shows six speed/deflection profiles 360–365, corresponding, respectively, to the depth of field characteristics of each of the 1×, 2×, 5×, 20×, 50×, and 100× lenses. The profiles relate the joystick deflection proportion to the focus axis speed in millimeters per second to emphasize that a maximum transport speed is independent of the selected lens, while the speed changes smoothly throughout the control range. As shown, each of the profiles approaches a common top speed (a.k.a. transport speed) of 100 millimeters per second, which generally occurs at the full joystick deflection proportion of 1.

As described above, the focus of the vision system is related to the depth of field, which is typically much shorter than the width of the display, and thus the transport speed in the focus range (i.e., Z-range) may be less than the transport speed for moving in the X-Y range. However, in the present examples of FIGS. 5A and 6A, the transport speed of 100 mm per second is the same as that shown for the X-Y speed in FIGS. 3A and 4A. FIG. 5B shows six image change rate/deflection curves 330–335, and FIG. 6B shows six image change rate/deflection curves 370–375, corresponding, respectively, to the depth of field characteristics of each of the 1×, 2×, 5×, 20×, 50×, and 100× lenses. The curves show the results of the speed/deflection profiles of the corresponding lenses of FIGS. 5A and 6A, respectively. The curves relate the joystick deflection proportion to an image change rate along the focus axis in terms of numbers of depths of field (DOF) per second, to emphasize an image change rate that is one important ergonomic factor. It should be appreciated that the curves show that over a substantial range of smaller deflections used for relatively precise control, the image change rate of the focus through the magnifying objective of the vision system is similar for a given joystick deflection, regardless of the selected lens. That is, the image will blur and/or focus at approximately same rate for a given joystick deflection, regardless of the selected lens. Generally, this substantial range includes and exceeds the deflections and/or speeds that might be used during relatively precise focusing or searching operations by a user. At larger deflections the increase in image change rate will vary as needed to reach the desired maximum Z axis transport speed.

The differences between the profiles and results of FIGS. 5A–5B and FIGS. 6A–6B should be appreciated. By using the third power of deflection of Equation 10 and setting N=1 to generate the profiles and results of FIGS. 5A–5B, the range of smaller deflections wherein the image change rate (the focus/blur rate) is approximately the same for given deflection regardless of the lens chosen is relatively reduced, while the transition to the transport speed is made somewhat smoother for higher magnifications. In contrast, by using the fourth power of deflection of Equation 11 and setting N=2 to generate the profiles and results of FIGS. 6A–6B, the range of smaller deflections wherein the image change rate (the focus/blur rate) is approximately the same for given deflection regardless of the lens chosen is relatively increased, while the transition to the transport speed is made a bit sharper for higher magnifications. However, more generally, it should be appreciated that other profiles according to the principles of this invention may be generated by setting N equal to other values greater than zero and N is not restricted to integer values. Furthermore, it should be appreciated that the exponent "3" on the first deflection δ in Equation 10 and the exponent "4" on the first occurrence of deflection δ in Equation 11 could more generally be any values greater than 1, and are not restricted to integer values. As previously discussed, the choice between such tradeoffs is made based on ergonomic experiments and user personal preferences.

In various exemplary embodiments according to this invention, the various exemplary equations and/or exemplary parameters described above provide exemplary robust and readily adaptable methods of generating ergonomically favorable speed/deflection profiles based on selected lens characteristics. However, more generally, it should be appreciated that the general behavior of the profiles and results of FIGS. 3A–3D, 4A–4D, 5A–5B and 6A–6B are ergonomically desirable regardless of the method of generating such profiles and results. More generally, numerous other equations and appropriate parameter values can be developed to generate similar or even indistinguishable speed/deflection profiles and results according to various appropriate lens characteristics. Thus, the particular equations and parameters disclosed herein are exemplary only, and not limiting. It should be further appreciated that in various exemplary embodiments, joystick deflection may be converted by speed/deflection profiles according to this invention by any of a variety of software and/or hardware methods, including the use of lookup tables, algorithmic conversion, or the like, or any other now known of later developed method of converting joystick deflection values to signals usable in a motion control system.

It will be appreciated that the disclosed method for converting joystick deflection into motion is advantageous in that the system considers lens characteristics at small joystick deflections which typically occur during ostensible precision maneuvers, but also "ignores" lens characteristics and moves rapidly (for providing fast long-range traverses) for large joystick deflections. In addition, ergonomic consistency can be provided, especially in the range of deflections most appropriate for relatively precise operations.

While the preferred embodiment of the invention has been illustrated and described, it will be appreciated that various changes can be made therein without departing from the spirit and scope of the invention.

The invention claimed is:

1. A magnified vision system comprising an imaging system and a workpiece stage, the imaging system and the workpiece stage capable of relative motion along at least one axis, the magnified vision system further comprising:
   a plurality of lenses interchangeable in the imaging system, the lenses having lens characteristics;
   a motion control system for providing the relative motion between the imaging system and the workpiece stage along the at least one axis;
   an input device including at least one element having a manually controllable deflection usable to adjust the relative motion along the at least one axis; and
   a deflection converter portion operable such that:
   for a given present deflection within a relatively lower range of deflections the magnified vision system provides a image change rate in an image from a present lens that is substantially similar to the respective image change rate provided when a different respective one of the lenses is the present lens; and
   for a given present deflection within a relatively higher range of deflections, the magnified vision system provides a speed of relative motion corresponding to the present lens such that for increasingly larger deflections in the higher range of deflections the speed of relative motion corresponding to the present lens becomes increasingly similar to the respective speed of relative motion provided when the different respective one of the lenses is the present lens.

2. The magnified vision system of claim 1, wherein the deflection converter portion is further operable such that over at least a lower part of a middle range of deflections between the relatively lower range of deflections and the relatively higher range of deflections, at increasingly larger deflections both the speed of relative motion corresponding to the present lens and the image change rate in an image from the present lens become less similar to the respective image change and the respective speed of relative motion provided when a different respective one of the lenses is the present lens.

3. The magnified vision system of claim 2, wherein the lower part of the middle range of deflections comprises deflections between 0.5 and 0.8 times the full deflection range.

4. The magnified vision system of claim 1, wherein the relatively lower range of deflections comprises deflections from zero up to at least 0.2 times the full deflection range.

5. The magnified vision system of claim 4, wherein the relatively lower range of deflections comprises deflections from zero up to at least 0.3 times the full deflection range.

6. The magnified vision system of claim 1, wherein the at least one axis comprises at least one axis parallel to a focal plane of the imaging system and the image change rate is comprises the rate at which an image feature travels across at least one of a visual field and a camera field of view and a video display of an image.

7. The magnified vision system of claim 1, wherein the at least one axis comprises an axis parallel to a focusing axis of the imaging system and the image change rate comprises the rate of change of the focus of an image as seen in at least one of a visual field and a camera field of view and a video display of an image.

8. The magnified vision system of claim 1, wherein at a maximum deflection in the relatively higher range of deflections the magnified vision system provides a speed of relative motion corresponding to the present lens that is the same as the respective speed of relative motion provided when the different respective one of the lenses is the present lens.

9. The magnified vision system of claim 1, wherein the different respective one of the lenses comprises each of the plurality of lenses.

10. The magnified vision system of claim 1, wherein the plurality of lenses comprises a plurality of configurations of a zoom lens.

11. A method for controlling the speed of a magnified vision system comprising an imaging system and a workpiece stage, the imaging system and the workpiece stage capable of relative motion along at least one axis, the magnified vision system further comprising:
    a plurality of lenses interchangeable in the imaging system, the lenses having lens characteristics;
    a motion control system for providing the relative motion between the imaging system and the workpiece stage along the at least one axis;
    an input device including at least one element having a manually controllable deflection usable to adjust the relative motion along the at least one axis; and
    a deflection converter portion;
    the method comprising:
    determining a present lens of the machine vision system;
    determining a present deflection of the machine vision system; and
    operating the magnified vision system based on the present deflection and the present lens such that:
    for a given present deflection within a relatively lower range of deflections the magnified vision system provides a image change rate in an image from the present lens that is substantially similar to the respective image change rate provided when a different respective one of the lenses is the present lens; and
    for a given present deflection within a relatively higher range of deflections, the magnified vision system provides a speed of relative motion corresponding to the present lens such that for increasingly larger deflections in the higher range of deflections the speed of relative motion corresponding to the present lens becomes increasingly similar to the respective speed of relative motion provided when a different respective one of the lenses is the present lens.

12. The method of claim 11, wherein operating the magnified vision system based on the present deflection and the present lens comprises operating the magnified vision system corresponding to a speed/deflection profile that corresponds to a present lens characteristic of the present lens, the speed deflection profile describable by a function that depends relatively strongly on the present lens characteristic at relatively lower deflections and depends relatively weakly on the present lens characteristic as the deflection approaches a maximum deflection.

13. The method of claim 12, wherein the dependence of the function on the present lens characteristic changes relatively smoothly between the relatively lower deflections and the deflections that approach the maximum deflection.

14. The method of claim 12, wherein the speed/deflection profile for any present lens corresponds substantially to a function of the form: $V(\delta, L) = (\delta^K V_{max})/[L - (|\delta|^N (L - L_{baseline}))]$, where V is the speed of relative motion along the at least one axis, $\delta$ is the deflection, L is the value of a current lens characteristic, K is a value greater than 1, $V_{max}$ is the value of a maximum speed of relative motion along the at least one axis, N is a value greater than 0, and $L_{baseline}$ is a constant value of a reference lens characteristic.

15. The method of claim 12, wherein the at least one axis comprises at least one axis parallel to a focal plane of the imaging system and the present lens characteristic is related to a magnification of the present lens.

16. The method of claim 12, wherein the at least one axis comprises an axis parallel to a focusing axis of the imaging system the present lens characteristics is related to a depth of field of the present lens.

17. The method of claim 11, the method further comprising manually deflecting the at least one element of the input device to a present deflection, and wherein at least one of determining a present lens of the machine vision system and determining a present deflection of the machine vision system and operating the magnified vision system based on the present deflection and the present lens is performed automatically according to a control software and/or hardware that controls the operations of the magnified vision system.

18. The method of claim 11, wherein the plurality of lenses comprises a plurality of configurations of a zoom lens.

19. A magnified vision system comprising an imaging system and a workpiece stage, the imaging system and the workpiece stage capable of relative motion along at least one axis, the magnified vision system further comprising:
 a plurality of lenses interchangeable in the imaging system, the lenses having lens characteristics;
 a motion control system for providing the relative motion between the imaging system and the workpiece stage along the at least one axis;
 an input device including at least one element having a manually controllable deflection usable to adjust the relative motion along the at least one axis; and
 a deflection converter portion operable such that:
 for a first deflection within a relatively lower range of deflections the magnified vision system provides a first image change rate in an image from a first lens that corresponds to a first speed of relative motion;
 for the first deflection the magnified vision system provides a second image change rate in an image from a second lens that corresponds to a second speed of relative motion such that the ratio of the greater of the first and second image changes rates to the lesser of the first and second image change rates is less that the ratio of the greater of the first and second speeds of relative motion to the lesser of the first and second speeds of relative motion; and
 for a plurality of deflections within a relatively higher range of deflections, the magnified vision system provides first respective speeds of relative motion corresponding to the first lens and second respective speeds of relative motion corresponding to the second lens such that for increasingly larger deflections in the plurality of deflections in the higher range of deflections the first respective speeds of relative motion converge toward the second respective speeds of relative motion.

20. The method of claim 19, wherein for the first deflection the ratio of the value of a lens characteristic of the first lens to the value of a comparable lens characteristic of the second lens is approximately the same as the ratio of the value of the speed of relative motion corresponding to the second image change rate to the speed of relative motion corresponding to the first image change rate.

* * * * *

UNITED STATES PATENT AND TRADEMARK OFFICE
CERTIFICATE OF CORRECTION

PATENT NO. : 7,106,300 B2  
APPLICATION NO. : 10/195689  
DATED : September 12, 2006  
INVENTOR(S) : B.E. Saylor et al.

It is certified that error appears in the above-identified patent and that said Letters Patent is hereby corrected as shown below:

|  | LINE | ERROR |
|---|---|---|
| On the Title Page Item (57) Pg. 1, col. 2 | Abstract 2 of text | "a image" should read --an image-- |
| On the Title Page Item (57) Pg. 1, col. 2 | Abstract 5 of text | "corresponds a present lens characteristics" should read --corresponds to present lens characteristics-- |
| On the Title Page Item (57) Pg. 1, col. 2 | Abstract 9 of text | "depends on relatively weakly on" should read --depends relatively weakly on-- |
| Column 13 (Claim 1, | 17 line 16) | "a image" should read --an image-- |
| Column 13 (Claim 6, | 24 line 3) | "change rate is comprises" should read --change rate comprises-- |
| Column 14 (Claim 11, | 24 line 15) | "do not indent "the method comprising:" |
| Column 14 (Claim 11, | 32 line 23) | "a image" should read --an image-- |
| Column 15 (Claim 16, | 7 line 3) | after "system" insert --and-- |
| Column 15 (Claim 16, | 7 line 3) | "the present lens characteristics is" should read --the present lens characteristic is-- |

UNITED STATES PATENT AND TRADEMARK OFFICE
CERTIFICATE OF CORRECTION

PATENT NO. : 7,106,300 B2
APPLICATION NO. : 10/195689
DATED : September 12, 2006
INVENTOR(S) : B.E. Saylor et al.

It is certified that error appears in the above-identified patent and that said Letters Patent is hereby corrected as shown below:

|  | LINE | ERROR |
|---|---|---|
| Column 15 (Claim 16, | 7 line 3) | "characteristics is" should read --characteristics are-- |
| Column 16 (Claim 19, | 10 line 22) | "changes rates" should read --change rate-- |
| Column 16 (Claim 19, | 11 line 23) | "less that the" should read --less than the-- |
| Column 16 (Claim 20, | 30 line 6) | before "speed" insert --value of the-- |

Signed and Sealed this

Twenty-fourth Day of June, 2008

JON W. DUDAS
*Director of the United States Patent and Trademark Office*